US008919609B2

(12) United States Patent
Wang et al.

(10) Patent No.: US 8,919,609 B2
(45) Date of Patent: Dec. 30, 2014

(54) DENTAL MIXING DEVICE HAVING AN AUTO-ALIGNING TIP MIXING TIP

(71) Applicant: Pac-Dent International, Inc., Walnut, CA (US)

(72) Inventors: Daniel Wang, Royland Heights, CA (US); Taosheng Hu, Jiangsu (CN); Bo Tao, Chino, CA (US); Bo Yue, Jiangsu (CN); Congbo Wei, Jiangsu (CN)

(*) Notice: Subject to any disclaimer, the term of this patent is extended or adjusted under 35 U.S.C. 154(b) by 19 days.

(21) Appl. No.: 13/736,412

(22) Filed: Jan. 8, 2013

(65) Prior Publication Data

US 2013/0177870 A1 Jul. 11, 2013

Related U.S. Application Data

(60) Provisional application No. 61/585,130, filed on Jan. 10, 2012.

(51) Int. Cl.
*B67D 7/78* (2010.01)
*A61C 5/06* (2006.01)

(52) U.S. Cl.
CPC .................. *A61C 5/064* (2013.01); *A61C 5/068* (2013.01)
USPC ......... 222/145.6; 222/137; 222/326; 222/386

(58) Field of Classification Search
CPC .......... A61C 5/06; A61C 5/062; A61C 5/064; A61C 5/068; A61J 1/2093; A61M 3/005; A61M 5/19; A61M 5/2448; A61M 5/3134; A61M 5/31596; A61M 5/34–5/348; B65D 81/325; B65D 81/3227
USPC .............. 222/132, 136, 137, 145.6, 325–327, 222/386, 568; 433/89, 90; 604/82, 191
See application file for complete search history.

(56) References Cited

U.S. PATENT DOCUMENTS

| | | | |
|---|---|---|---|
| 3,491,757 A * | 1/1970 | Arce | 604/242 |
| 4,538,920 A | 9/1985 | Drake | |
| 4,753,536 A | 6/1988 | Spehar et al. | |
| 4,771,919 A * | 9/1988 | Ernst | 222/134 |
| 4,974,756 A * | 12/1990 | Pearson et al. | 222/562 |
| 4,978,336 A * | 12/1990 | Capozzi et al. | 604/82 |
| 4,995,540 A * | 2/1991 | Colin et al. | 222/132 |
| 5,033,650 A * | 7/1991 | Colin et al. | 222/137 |
| 5,487,606 A * | 1/1996 | Keller | 366/339 |
| 5,918,772 A | 7/1999 | Keller et al. | |
| 6,135,631 A * | 10/2000 | Keller | 366/339 |
| 6,328,182 B1 * | 12/2001 | Brugner | 222/145.6 |
| 6,796,961 B1 * | 9/2004 | Hsu | 604/110 |
| 6,874,657 B2 * | 4/2005 | Metzner et al. | 222/82 |

(Continued)

*Primary Examiner* — Patrick M Buechner
(74) *Attorney, Agent, or Firm* — Mandour & Associates, APC

(57) ABSTRACT

A dental mixing device with a barrel, a mixing tip, and a plunger. The plunger moves dental material through the barrel where it is mixed using a mixing tip. The mixing tip includes an auto-aligning fitting female element configured to align with an auto-aligning fitting male element of the barrel. This auto-alignment simplifies the attachment between the mixing tip and the barrel. The mixing tip also includes a seal component with a soft material (or component) to insert into the auto-aligning fitting element which is a hard material (or component) to achieve a seal. The seal component and auto-alignment fitting element can be combined together into one component instead of two components.

10 Claims, 4 Drawing Sheets

(56) References Cited

U.S. PATENT DOCUMENTS

| | | | |
|---|---|---|---|
| 2007/0166660 A1* | 7/2007 | Peuker et al. | 433/89 |
| 2007/0175921 A1* | 8/2007 | Keller | 222/137 |
| 2009/0134186 A1* | 5/2009 | Keller | 222/137 |
| 2009/0152300 A1* | 6/2009 | Hayman et al. | 222/145.6 |
| 2010/0102088 A1* | 4/2010 | Keller | 222/137 |
| 2010/0256591 A1* | 10/2010 | Ho et al. | 604/415 |
| 2011/0198370 A1 | 8/2011 | Ho et al. | |

* cited by examiner

DENTAL MIXING DEVICE HAVING AN AUTO-ALIGNING TIP MIXING TIP

CROSS REFERENCE TO RELATED APPLICATIONS

This application claims priority under 35 U.S.C. §119(e) to U.S. Provisional Application No. 61/585,130, filed Jan. 10, 2012, and entitled "Dispensing syringe having multiple barrels and mixing apparatus," the disclosure of which is hereby incorporated by reference in its entirety.

BACKGROUND OF THE INVENTION

1. Field of Invention

The present invention relates generally to mixing dual and multi component dental materials in dentistry procedures, and specifically to an improved dental mixing device.

2. Description of Related Art

There are many dental procedures that require the mixing of two or more dental materials (also known as compositions, compounds, and substances) before the mixed dental material can be used in that particular dental procedure. In the past, a common practice was to measure the separate dental materials, drop them into a mixing dish, mix the dental materials together using an applicator brush, and then use the applicator brush to apply the mixed dental materials to the desired teeth surfaces. However, mixing using the applicator brush led to a host of problems including being tedious, time consuming, causing contamination from the patient's saliva, and having dental material evaporate or harden. For example, when bleaching teeth using peroxide, the peroxide will decompose immediately after mixing.

In view of such problems, auto-mixing dental mixing devices such as a dispensing syringe (also known as a double barrel syringe) were developed to address these problems. In general, dispensing syringes include two separate, elongated barrels (also known as chambers) that are arranged in a side-by-side configuration. The barrels are sealed, and the base paste is stored in one barrel, while the catalyst paste is stored in the other barrel. The barrels are connected to a dispensing tip.

In practice, the user, which is typically a dentist, pushes on the plunger of the syringe to force the base and catalyst pastes from their respective barrels and into the dispensing tip. The dispensing tip typically contains a static mixer. As the base and catalyst pastes are extruded through the static mixer, they are combined and mixed together to form the final, mixed dental cement. Then, the dentist can dispense the cement onto the desired target, for example, a temporary crown, and mount the crown over a crown-prepped tooth in the mouth of the patient. Dispensing syringes are used in dentistry for storing, mixing, and dispensing a wide variety of dental materials such as whiting gels, impression materials, dental filling materials temporary dental restoration materials, cements, and adhesives.

One example of a dispensing syringe is illustrated in Drake, U.S. Pat. No. 4,538,920. Drake discloses a dispensing device having a having a pair of chambers for storing dental resins separately and a pair of plungers that are forced into the chambers to discharge the resins. The device further includes a static-mixing element housed with an exit conduit and a discharge nozzle. The static-mixing element is held in a fixed position in order to maintain a predetermined alignment of a first blade in the static-mixing element relative to the two streams of resinous material.

Another example of a dispensing syringe is illustrated in Spehar et al., U.S. Pat. No. 4,753,536. Spehar discloses a double barrel syringe having two compartments for storing two separate dental polymeric materials, a discharge assembly, and a nozzle assembly for dispensing the material. The nozzle assembly comprises a common nozzle, a static-mixing element with an arm extending from one end. The static mixer is arbitrarily inserted into the bore of the nozzle. The discharge of the polymeric material from the compartments causes the static mixer to turn until the arm engages an end stop. The end stop prevents further rotation of the arm as material is fed into the nozzle, thereby allowing the mixer to intermix the two materials from the storage compartments.

Dentists often prefer working with these types of auto-mixing devices, such as dispensing syringes, because the base and catalyst pastes are stored in commercially-available cartridges and can be dispensed from the cartridges in a predetermined volume ratio to form an optimally mixed composition. Thus, the dentist can save time using such auto-mixing devices and avoid mixing ratio errors.

However, the prior art falls short of truly simplifying the auto-mixing process. Prior to the use of a dispensing syringe, the mixing tip must be connected to the dual barrel container. This is because mixing tips are typically designed for a single use, since after one use the dental material hardens into cement within the tip such that the mixing tip cannot be reused. When the dentist wants to connect a new mixing tip to a dual barrel container, the dentist must pay close attention to align the outlets of the dual barrel container with the inlets of the mixing tip, along with paying attention to any other connection means (e.g., seal, threads, etc.). This alignment takes time, effort, and can be frustrating. Since this connection is typically performed while working with a dental patient, when time is of the essence, it is important that this connection be made quickly. Also, it is critical that the dentist's attention not be distracted from the dental procedure on hand.

Conventional devices exist to help fasten the mixing tip to the barrel, but do not simplify the attachment process. For example, U.S. Pat. No. 5,918,772 issued to Keller et al. discloses a bayonet fastening device for the attachment of an accessory to a multiple component cartridge or dispensing device. The bayonet attachment on the cartridge for attaching a mixer or accessory to a multiple component cartridge is formed as a ring-shaped bayonet socket with two internal recesses and two diametrically opposed cutouts forming one bayonet coupling part means, whereas the bayonet attachment of the mixer or accessory comprises two bayonet lugs corresponding to the cutouts. In a preferred embodiment the lugs and cutouts are of different widths for the coded alignment of the mixer or accessory to the cartridge in one predetermined position only.

U.S. Pat. Pub. No. 2011/0198,370 to Ho et al. discloses a device for mixing and discharging plural materials. The device for mixing and discharging plural materials has a body, a housing and a sealing plug. The body has multiple barrels and multiple tubes communicating with the barrels. The housing is rotatably attached to the body in a thread manner and has a mixing chamber and a discharging segment. The sealing plug is mounted in the mixing chamber to seal the tubes and has a sealing disk and multiple sealing sleeves.

Keller and Ho fall short because they do not simplify the alignment between the barrel and the tip. Instead, they tighten a connection that is already established. Kelly and Ho still require the user to carefully align the mixer's base/tip with the cartridge's outlets during installation. Additionally, Kelly and Ho lack a combination of hard and soft materials of a mixer and syringe tip that ensure a perfect seal and prevent cross contamination.

SUMMARY OF THE INVENTION

The present invention includes an improved dental mixing device with a barrel, a mixing tip, and a plunger. The plunger moves dental material through the barrel where it is mixed using a mixing tip. The mixing tip includes an auto-aligning fitting female element configured to align with an auto-aligning fitting male element of the barrel. This auto-alignment simplifies the attachment between the mixing tip and the barrel, saving the user the time and effort. The mixing tip also includes a seal component with a soft material (or component) to insert into the auto-aligning fitting element which is a hard material (or component) to achieve an ideal seal. The seal component and auto-alignment fitting element can be combined together into one component instead of two components.

An advantage of the present invention is that the assembly easier for the user by eliminating the need to align the mixing tip's inlet and the container barrel's outlet. The invention accomplishes this by having an auto-matching, auto-aligning, auto-locking structure such that no aiming or aligning is required.

Auto-matching refers to the screw thread-based mechanism between the barrel and the syringe in such a way that does not require the user to carefully and purposefully match the barrel and the syringe together during installation. The screw thread-based mechanism can be, for example, a luer-lock or a non-luer-lock, can be a single thread or multi-thread. Auto-aligning refers to the one or more raised ridges located in between the syringe outlets and one or more grooves on the syringe's internal sealing component that work in tandem to automatically align the ridges with the grooves during installation. The shapes of the raised edges and grooves could be different cosmetically from each other. Exemplary shapes include slotted, cross, hexagon, triangle, square, rectangle, circle, ellipse, star, trapezoid, etc.

Another advantage of the present invention is that hard and soft materials are used together in the female fitting element and the seal of the mixing tip to better seal the device. The hard/soft feature in the device is a novel feature of the present invention. Conventional sealing typically relies on a hard plastic sealing, which theoretically, cannot be a perfect seal. The fact that a soft material is able to shrink and expand depending on the applied force makes it the ideal material for a perfect seal, but using just soft material alone will not work because it still needs the support from the hard material, making the hard/soft combination a unique advantage of the present invention. The soft material could, for example, be over-molded onto the hard material making the female fitting element and the sealing component into one component. In another embodiment, the hard and soft materials are separate components.

The foregoing, and other features and advantages of the invention, will be apparent from the following, more particular description of the preferred embodiments of the invention, the accompanying drawings, and the claims.

DETAILED DESCRIPTION OF THE INVENTION

Figure 1:
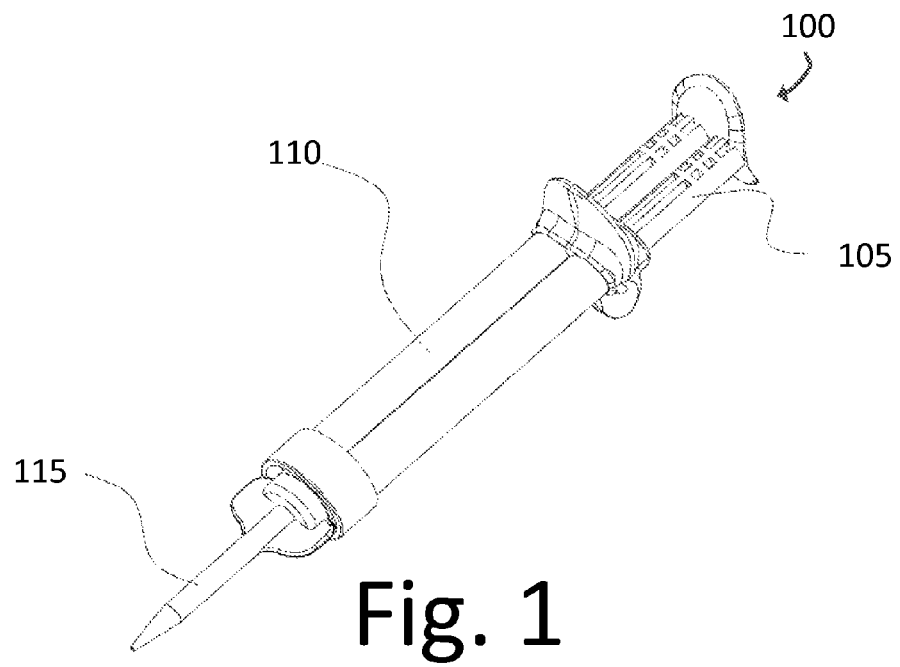
FIG. 1 illustrates a perspective view of a dental mixing device according to one embodiment of the invention.

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

Further features and advantages of the invention, as well as the structure and operation of various embodiments of the invention, are described in detail below with reference to the accompanying FIGS. 1-6, wherein like reference numerals refer to like elements. Although the illustrations illustrate a dual barrel dental mixing device, one with skill in the art could add an additional barrel (referred to herein as a multi-barrel mixing device) or use the dental mixing device outside of the dental industry.

The present invention includes an improved barrel mixing device. The device includes a mixing tip, a barrel, and a plunger. The plunger moves the material through the barrel. The barrel can be dual or multi (e.g., more than two) barrel containers. The mixing tip includes a novel connection structure for simplifying the process of connecting a mixing tip with a dual barrel container. The mixing tip has an auto-aligning fitting female element having a split slot configured to connect with a protruding dam of an auto-aligning fitting male element of the dual barrel container. This auto-aligning fitting female element also includes a locating block configured to fit into a locating slot of the dual barrel to ensure the mixing tip is aligned correctly with the barrel. The novel seal component provides a soft material to insert the hard material of the auto-aligning fitting female element to achieve an ideal seal.

The device has several distinctive features. For example, the device has a unique auto-aligning/auto-matching design that no longer requires the user to carefully align the mixer's syringe with the cartridge's outlets during installation. Additionally, the device includes internal sealing and female fitting components that include both hard and soft materials which guarantees a perfect seal every time. Also, the device's syringe tip end has a ridged wall that separates the outlets of the multi-barrels, and works in tandem with the sealing component's groove, which is covered by soft material, to effectively prevent chemicals inside the multi-barrel syringe from cross-contamination during storage and dispensing.

FIG. 1 illustrates a perspective view of a dental mixing device 100 according to one embodiment of the invention. The device 100 (e.g., dual barrel syringe) includes a mixing tip 115, a barrel 110, and a plunger 105. The device 100 can be used in the dental field for storing, mixing, and dispensing of dental materials including whitening gels, impression materials, filling materials, temporary dental restoration materials, etc. The plunger 105 pushes the dental material through the barrel 110 and into the mixing tip 115.

The barrel 110 (e.g., dual barrels, multi-barrel container, etc.) stores dental materials prior to mixing. The barrel 110 includes at least two dental materials separated by different parallel chambers, and the chambers having inlets at one end and outlets at the other end. The inlets are for filling the materials and the outlets are for dispensing the material into the mixing tip. The outlet of the barrel 110 connects with a connector on the mixing tip 115. The barrel 110 may have a male/female threaded coupling which matches with the mixing tip's female/male threaded coupling, such as a luer lock.

The mixing tip 115 is configured to receive a plurality of materials and mix them prior to the dental procedure. The mixing tip 115 has a mixing element and a connector which connects with the barrel's outlet. The connector of the mixing tip 115 includes a body, seal component(s) and separation element(s). The mixing tip 115 also has a threaded coupling which matches with the barrel 110. The mixing tip 115 also has a pattern on the outside to increase the grip friction force. The mixing tip 115 auto-matches, auto-aligns and auto-locks with the barrel 110 using the connector without the need to aim and align the components' outlets when connecting the mixing tip. A cutout region as part of the connector may include a flexible sealing element made of a soft plastic material with the result that dimensional and material elasticity is provided. The cutouts may be located at least partially in a hard plastic material of the connector. The cutout element may include welding surfaces that are in different planes and have a non-planar three-dimensional configuration.

Figure 2:
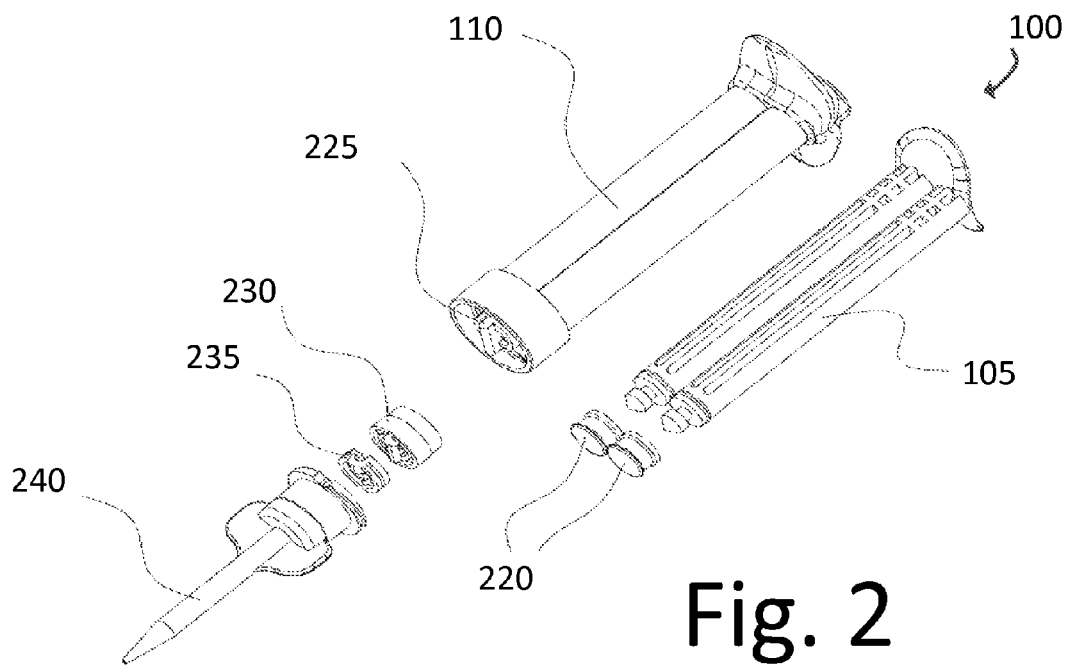
FIG. 2 illustrates an exploded view of the components of the device according to one embodiment of the invention.

FIG. 2 illustrates an exploded view of the components of the device 100 according to one embodiment of the invention. The plunger 105 can be a conventional plunger which is known by those with skill in the art. The plunger 105 can have a pressing means 220 for squeezing the dental material out of the barrel 110.

The barrel 110 (e.g., barrel containers) has an auto-aligning fitting male element 225 configured to align, apply pressure in parallel with the device 100, and lock together with the mixing tip 115.

The mixing tip 115 has an auto-aligning fitting female element 230, a seal component 235, and a syringe 240. The auto-aligning fitting female element 230 is used together with the auto-aligning fitting male element 225 to auto-align the mixing tip 115 and the barrel 110 to align to, attach with, and lock to the auto-aligning female element 230.

The auto-matching, auto-aligning, male and female fitting elements 225, 230 include an auto-positioning and auto-locking ridge, a matching auto-positioning and auto-locking slot, and can also feature a locating slot (also known as a locating dowel).

The seal component or components 235 are used with the female fitting element 230 for sealing the dental materials before they are dispensed into an inlet of the mixing tip 115. The female fitting element includes a hard material (e.g., plastic) and the seal component 235 includes a soft material to best attach to the syringe 240. The hard material of the female fitting element 230 is for inserting the mixing tip 115 onto the barrel 110. The soft material of the sealing component 235 is to achieve an ideal seal to prevent the dental material from leaking or cross-contaminating with each other prior to mixing. The attachment between the hard and soft material can be by over molding, adhesive, ultrasonic welding or other combination methods. The dental materials are separated by an auto-locking ridge and soft material components.

Further, at least one part of the connector (e.g., female fitting 230) may be made of a hard plastic material or may have a contact surface defined by the hard plastic material. The contact surface may provide connection with the barrel's outlet. The hard plastic material may be Polyoxymethylene (POM), Acrylonitrile butadiene styrene (ABS), or polypropylene (PE). The soft plastic material may be a thermoplastic Elastomer or Silicone.

Figure 3:
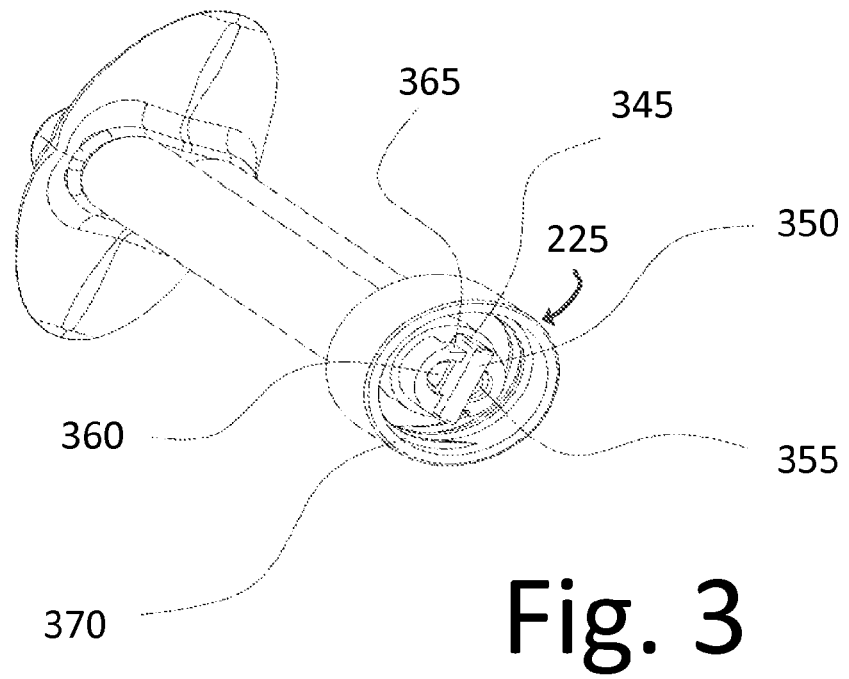
FIG. 3 illustrates an auto-aligning fitting male element of a barrel of the device according to one embodiment of the invention.

FIG. 3 illustrates the auto-aligning fitting male element 225 of the barrel 110 of the device 100 according to one embodiment of the invention. The auto-aligning fitting male element 225 includes a protruding dam 345 having a top 350, two outlets 355, 360, a locating slot 365, and a flange 370.

The protruding dam 345 having the top 350 provides the male portion of the auto-aligning fitting male element 225 and is configured to align with and insert into the auto-aligning fitting female element 220. The top 350 of the protruding dam 345 is used for keeping pressure on the auto-aligning fitting female element 230 to ensure the auto-aligning fitting female element 230 maintains in close contact with the seal component 235 of the mixing tip 115.

The protruding dam 345 is located between the outlets 355, 360 and keeps the two dental materials separate before the materials are dispensed into the mixing tip 115, preventing cross-contamination. The outlets 355, 360 are for the dental materials to pass through when the plunger 105 is pressed.

The locating slot 365 (e.g., locating dowel) ensures the barrel 110 can only be attached to the mixing tip 115 in one way. Further, the locating slot 365 locks the mixing tip 115 in place on barrel 110. The flange 370 is used to lock up the barrel 110 to the mixing tip 115 by screwing the flange 370 around the mixing tip's screw thread shown in FIG. 4.

Figure 4:
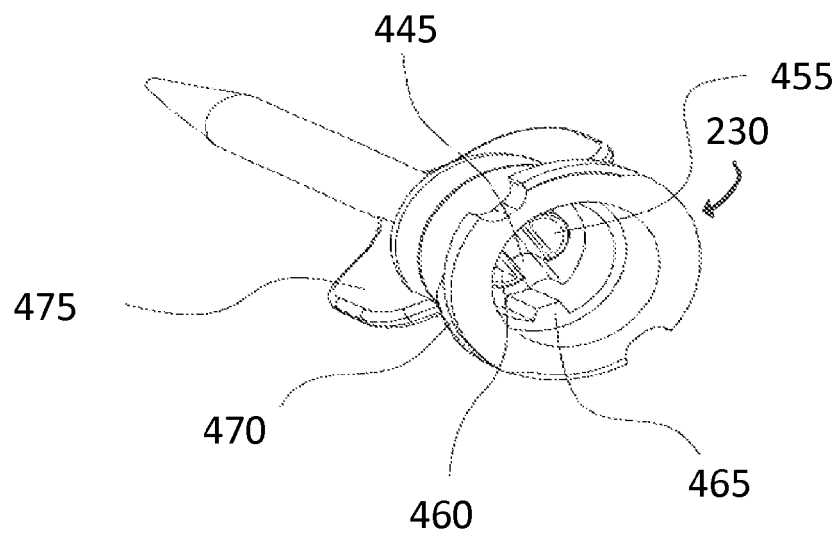
FIG. 4 illustrates an auto-aligning fitting female element of a mixing tip of the device according to one embodiment of the invention.

FIG. 4 illustrates the auto-aligning fitting female element 230 of the mixing tip 115 of the device 100 according to one embodiment of the invention. Corresponding with the auto-aligning fitting male element 225, the auto-aligning fitting female element 230 of the mixing tip 115 has a split slot 445, two inlets 455, 460, a locating block 465, and a screw thread 470. The mixing tip 115 also has a handle 475.

The split slot 445 is configured to receive and mate with the top 350 of the protruding dam 345 when the flange 370 is screwed onto the screw thread 470. The inlets 455, 460 are configured to mate with the outlets 355, 360 and receive the dental materials passed through the outlets 355, 360. The locating block 465 is configured to fit into the locating slot 365 to ensure there is only one way for the mixing tip 115 to be positioned on the barrel 110. The screw thread 470 is configured to match and receive the flange 370. The handle 475 allows the dentist to guide and control the syringe 240 and allows for secure gripping when screwing and tightening the flange 370.

Figure 5:
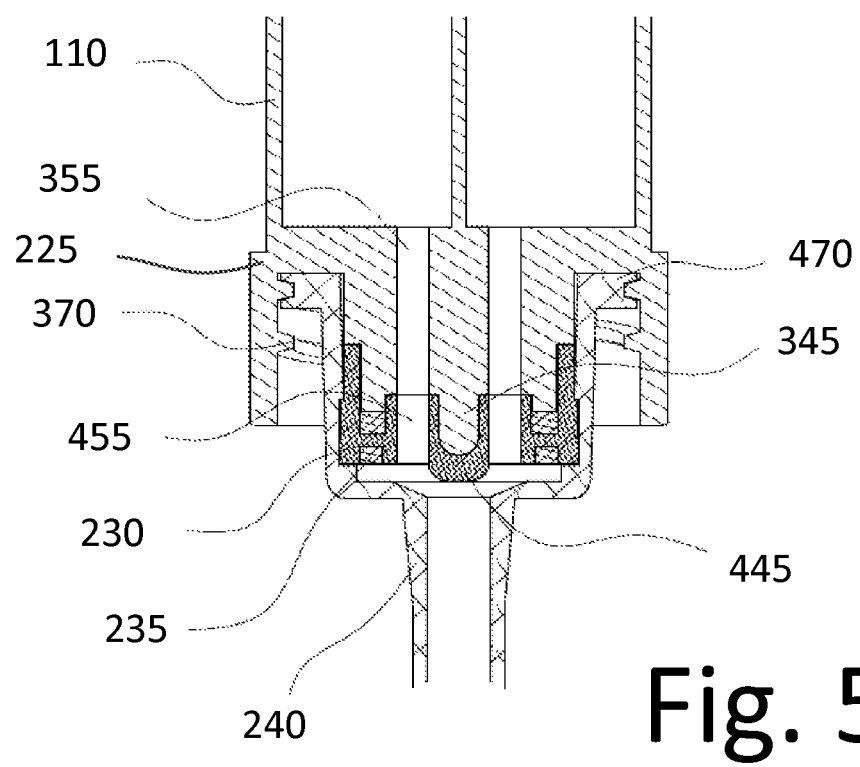
FIG. 5 illustrates a sectional view illustrating the attachment of the male and auto-aligning fitting female elements of the device according to one embodiment of the invention.

FIG. 5 illustrates a sectional view illustrating the attachment of the male and female auto-aligning fitting elements 225, 230 of the device 100 according to one embodiment of the invention. FIG. 5 illustrates the alignment between the barrel 110 and the mixing tip 115. The barrel 110 has the protruding dam 345, outlets 355, 360, and the flange 370. The mixing tip 115 has the split slot 445, inlets 355, 360, screw thread 470, seal component 235, and syringe 240.

Figure 6:
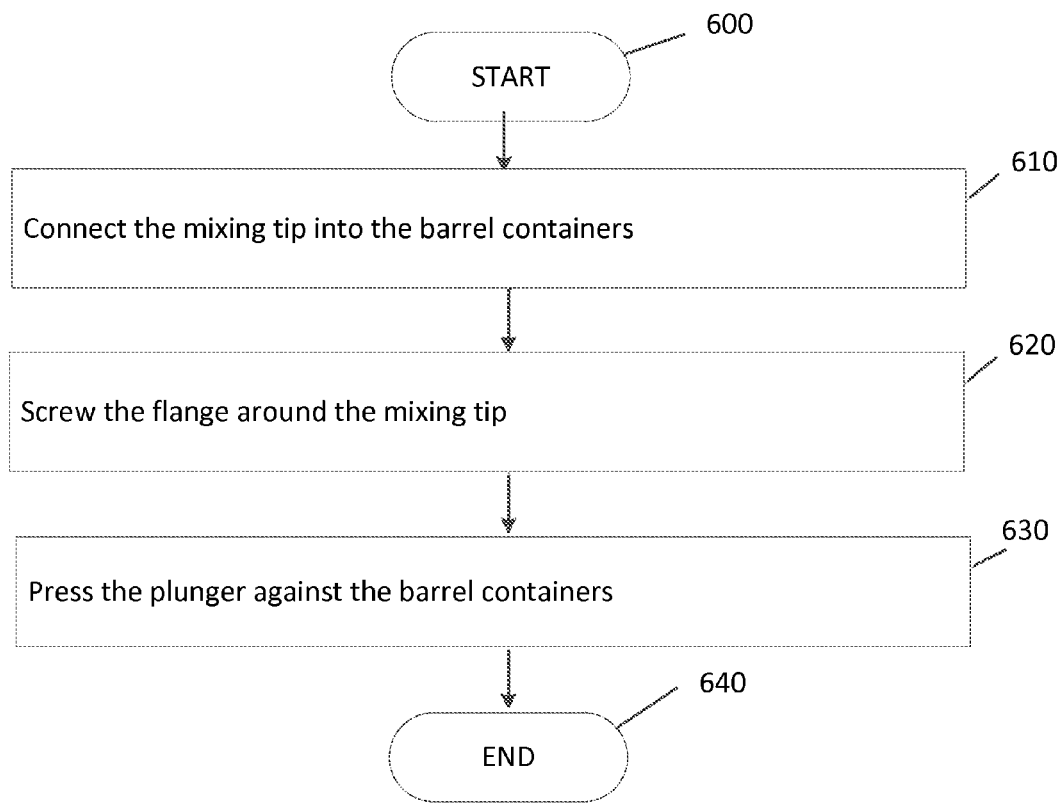
FIG. 6 illustrates a flow chart showing a process for connecting the device according to an embodiment of the invention.

FIG. 6 illustrates a flow chart showing a process for connecting the device 100 according to an embodiment of the invention. The process starts at step 600. At step 610, the user connects the mixing tip 115 into the barrel 110. When tightening the mixing tip 115 onto the barrel 110, the auto-aligning fitting male element 225 will first contact the split slot 445, which auto-aligns the screw thread 470 and the flange 370.

At step 620, the user screws the flange 370 around the mixing tip 115. This tightens the connection between the mixing tip 115 and the barrel 110 and allows the protruding dam 345 to press the auto-aligning fitting female element 230 against the seal component 235. When screwing and tightening the mixing tip 115 onto the barrel 110, the inlets 455, 460 on the mixing tip 115 and the outlets 355, 360 on the barrel 110 will align and be sealed by the seal component 235. The protruding dam 345 applies tight pressure on the auto-aligning fitting female element 230. The user presses the plunger 105 against the barrel 110 at step 630. This squeezes the dental material through the mixing tip 115. The process ends at step 640.

It is to be recognized that depending on the embodiment, certain acts or events of any of the methods described herein can be performed in a different sequence, may be added, merged, or left out altogether (for example, not all described acts or events are necessary for the practice of the method). Moreover, in certain embodiments, acts or events may be performed concurrently, for example, through multi-threaded processing, interrupt processing, or multiple processors, rather than sequentially.

It should be understood that the invention is not limited to the embodiments set forth herein for purposes of exemplification, but is to be defined only by a fair reading of the appended claims, including the full range of equivalency to which each element thereof is entitled. Although the invention has been described with reference to the above examples, it will be understood that modifications and variations are encompassed within the spirit and scope of the invention. Accordingly, the invention is limited only by the following claims.

What is claimed is:

1. A device comprising:
   a plunger;
   a barrel attached to the plunger, the barrel configured to hold a first dental barrel holding a first dental material and a second dental barrel holding a second dental material, wherein the barrel comprises a male auto-aligning fitting element having a protruding dam;
   a mixing tip attached to the barrel, wherein the mixing tip comprising a female auto-aligning fitting element having a split slot, wherein the protruding dam of the male auto-aligning fitting element is configured to align with and press on the split slot of the female auto-aligning fitting element; and
   a seal component attached to the mixing tip, wherein the seal component is structured to match up with and insert into the female auto-aligning fitting element,
   wherein the seal component comprises a soft material and the female auto-aligning fitting element comprising a hard material, wherein the soft material of the seal component is configured to shrink and expand, wherein the soft material of the seal component shrinks upon receiving pressure from the hard material of the female auto-aligning fitting element.

2. The device of claim 1, wherein the mixing tip comprises a syringe.

3. The device of claim 1, wherein the protruding dam separates the first dental material and the second dental material.

4. The device of claim 1, wherein the hard material comprises plastic.

5. The device of claim 4, wherein the plastic comprises Polyoxymethylene, Acrylonitrile butadiene styrene, or polypropylene.

6. The device of claim 1, wherein the soft material comprises thermoplastic Elastomer or Silicone.

7. The device of claim 1, wherein the mixing tip comprises a male or female threaded coupling which mates with a coupling of the barrel.

8. The device of claim 1, wherein the seal component and the female auto-aligning fitting element are over-molded together into one component.

9. The device of claim 1, wherein the seal component and the female auto-aligning fitting element are two separate components configured to attach together.

10. The device of claim 1, wherein the barrel comprises a locating slot configured to align with a locating block on the mixing tip, wherein the locating slot and locating block create only one way to match the barrel to the mixing tip.

* * * * *